United States Patent [19]

McCarthy

[11] Patent Number: 5,169,976

[45] Date of Patent: Dec. 8, 1992

[54] N-(BIPHENYLMETHYL)-3-HYDROXY-GLUTARAMIC ACID AND DERIVATIVES AS HYPOCHOLESTEROLEMIC AGENTS

[75] Inventor: Peter A. McCarthy, Pawcatuck, Conn.

[73] Assignee: Pfizer Inc., New York, N.Y.

[21] Appl. No.: 487,948

[22] PCT Filed: Nov. 25, 1987

[86] PCT No.: PCT/US87/03140

§ 371 Date: May 3, 1990

§ 102(e) Date: May 3, 1990

[87] PCT Pub. No.: WO89/04821

PCT Pub. Date: Jun. 1, 1989

[51] Int. Cl.$^5$ .................. C07C 229/34; C07C 229/32
[52] U.S. Cl. ........................................ 560/39; 549/304; 549/305; 549/307; 549/321; 549/323; 549/324; 558/275; 558/276; 560/41; 562/444
[58] Field of Search .......................... 562/444; 560/39; 514/541, 563, 470, 471, 512; 549/304, 321; 558/275

[56] References Cited

U.S. PATENT DOCUMENTS

| 3,341,528 | 9/1967 | Shavel et al. | 260/240 |
| 4,198,425 | 4/1980 | Mitsui et al. | 424/279 |
| 4,375,475 | 3/1983 | Willard et al. | 424/279 |
| 4,459,422 | 7/1984 | Willard et al. | 560/59 |
| 4,603,145 | 7/1986 | DeVries et al. | 514/563 |
| 4,678,806 | 7/1987 | Baldwin et al. | 514/400 |
| 4,772,626 | 9/1988 | Smith et al. | 514/460 |
| 4,855,321 | 8/1989 | Smith et al. | 514/460 |

OTHER PUBLICATIONS

Stokker et al., J. Med. Chem., vol. 28, pp. 347-358 (1985).

Primary Examiner—Jose G. Dees
Assistant Examiner—B. Frazier
Attorney, Agent, or Firm—Peter C. Richardson; J. Trevor Lumb; D. Stuart McFarlin

[57] ABSTRACT

Variously substituted 4-(biphen-2-ylmethylcarbamoyl)-3-hydroxybutyric acids and esters, also named as N-(biphen-2-yl)-3-hydroxyglutaramic acid derivatives, are blood cholesterol lowering agents and so are useful in the prevention and treatment of cardiovascular diseases such as atherosclerosis.

11 Claims, No Drawings

N-(BIPHENYLMETHYL)-3-HYDROXY-GLUTARAMIC ACID AND DERIVATIVES AS HYPOCHOLESTEROLEMIC AGENTS

BACKGROUND OF THE INVENTION

Variously substituted N-(biphen-2-ylmethyl)-3-hydroxyglutaramic acid and derivatives, as defined by the formula (I) below (alternatively named as 4-(biphen-2-ylmethylcarbamoyl)-3-hydroxybutyric acid derivatives) possess hypocholesterolemic (blood cholesterol lowering) activity and so are useful in the prevention and treatment of certain cardiovascular diseases such as atherosclerosis.

Previously reported as hypocholesterolemic compounds have been variously substituted 6-phenyl-, 6-(2-phenethyl)-, 6-(3-phenylpropyl)- and 6-(2-styryl)-4-hydroxy-6-hexanolides including, in particular,

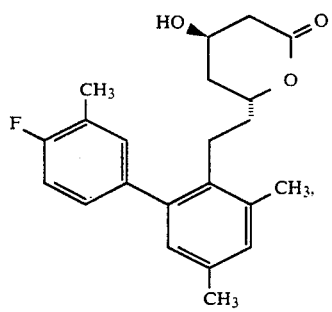

and the corresponding ring opened 3,5-dihydroxy-omega-substituted- (hexan-, heptan-, octan- and 6-hepten-)oic acids [Willard et al., U.S. Pat. Nos. 4,375,475 and 4,459,422; see also Mitsui et al., U.S. Pat. No. 4,198,425; Stokker et al., J. Med. Chem., vol. 28, pp. 347–358 (1985)].

SUMMARY OF THE INVENTION

The present invention is directed to hypocholesterolemic compounds having the formula

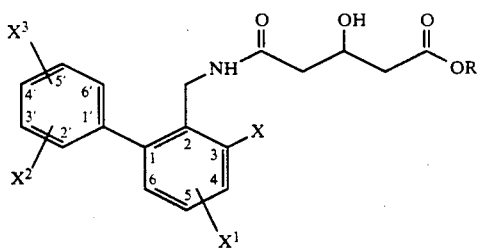

wherein
R is hydrogen, $(C_1-C_3)$alkyl, phenyl, benzyl or a conventional radical forming an ester group which is hydrolyzable under physiological conditions;

X is F, Cl, Br, I, $(C_1-C_3)$alkyl, $CF_3$, benzyl, $(C_1-C_3)$alkoxy, $(C_2-C_4)$alkanoyloxy or $(C_2-C_4)$alkoxycarbonyl; and $X^1$, $X^2$ and $X^3$ are each independently hydrogen, F, Cl, Br, I, $(C_1-C_3)$alkyl, $CF_3$, benzyl, $(C_1-C_3)$alkoxy, $(C_2-C_4)$alkanoyloxy or $(C_2-C_4)$alkoxycarbonyl; and the pharmaceutically-acceptable cationic salts thereof when R is hydrogen.

The depiction of the substituents X, $X^1$, $X^2$ and $X^3$ in the compound of the formula (I) is not intended to limit the substituents on each ring to two. Rather, while the substituent X is specifically substituted at the 3-position, it is intended that each of the remaining three substituents, if present, can be substituted at any open position on either phenyl ring. For example, all three of $X^1$, $X^2$ and $X^3$ are optionally substituted on one or the other of the phenyl rings.

The preferred compound, because of its ease of preparation and level of hypocholesterolemic activity, has R as hydrogen, and X, $X^1$ and $X^2$ as 3,3',5-trimethyl and $X^4$ as 4'-fluoro.

Pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as "pro-drugs". Such esters are now as well-known and common in the medicinal art as pharmaceutically-acceptable salts. Such esters are generally used to enhance oral absorption, but in any event are readily hydrolyzed in vivo to the parent acid. The more preferred ester forming radicals are those wherein R is:

furan-5(1H)-on-1-yl;
isobenzofuran-3(1H)-on-1-yl;
3,4-dihydrofuran-5(1 H)-on-1-yl;
—$CHR^1OCOR^2$; or
—$CHR^1OCOOR^2$;
wherein $R^1$ is hydrogen or methyl; and $R^2$ is $(C_1-C_6)$alkyl. The most preferred radicals are pivaloyloxymethyl and 1-(ethoxycarbonyloxy)ethyl.

The present invention also encompasses pharmaceutical compositions for the treatment or prevention of atherosclerosis in a mammal which comprises a blood cholesterol lowering effective amount of a compound of the formula (I); and method of treating or preventing atherosclerosis in a mammal which comprises administering a blood cholesterol lowering effective amount of a compound of the formula (I) to said mammal.

DETAILED DESCRIPTION OF THE INVENTION

The present invention is readily carried out. Thus, the hydroxy protected anhydride of 3-hydroxyglutaric anhydride (alternatively named 3-hydroxypentanedioic anhydride), e.g., 3-(t-butyldimethylsilyloxy)glutaric anhydride, is reacted with a diphen-2-ylamine of the formula

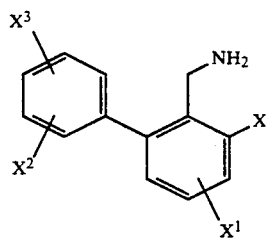

wherein X, $X^1$, $X^2$ and $X^3$ are as defined above, in the conventional manner long used to prepare half amides from amines and cyclic anhydrides. For example, see and Boyd, "Organic Chemistry", 3rd Ed., Allyn and Bacon, Inc., Boston, 1973, pp. 668–670, and the examples below. To assure maintenance of the hydroxy protecting group during the anhydride-amine reaction, basic conditions are generally maintained by using either an excess of the amine (i.e. at least 2 molar equivalents of amine relative to anhydride) or an excess of a tertiary amine (e.g., triethylamine, 4-dimethylaminopyridine; at least 1 molar equivalent thereof when substantially 1 molar equivalent of the amine reactant is employed). At the same time, reaction rate is generally enhanced by the presence of the excess amine reactant or tertiary amine. The reaction is generally carried out in a reaction-inert solvent, such as methylene chloride. As used herein, the term reaction-inert solvent refers to a solvent which does not interact with reactants, intermediates or products in a manner which adversely affects the yield of the desired product. Temperature is not critical, e.g., 0°-50° C., conveniently ambient temperatures, being generally satisfactory. If desired, in order to avoid undue exotherms, the reaction can be initiated at a lower temperature, e.g. 0° C. to −70° C., then brought to a higher temperature for completion of the reaction If the protecting group (e.g., t-butyldimethylsilyl) is not removed by acid hydrolysis during isolation, it can be removed in a separate step, in either case, involving conventional acid cleavage (e.g., with HF in CH$_3$CN as exemplified below) or conventional acid catalyzed hydrolysis or solvolysis, yielding an acid compound of the formula (I) wherein R is H.

By conventional modification of the isolation procedure, the compounds of the formula (I) wherein R is H are alternatively isolated in the form of a pharmaceutically-acceptable cationic salt, as defined above. Such salts are also readily prepared from the isolated acid forms by standard methods. For example, an equivalent of the corresponding cationic hydroxide, carbonate or bicarbonate, or of an amine, is combined with the carboxylic acid in an organic or aqueous solvent. The salt is isolated by concentration and/or the addition of a non-solvent.

The (C$_1$-C$_3$)alkyl, phenyl and benzyl esters encompassed by the formula (I) are also readily prepared from the acid forms by conventional methods. In those methods which involve reaction of an activated form of acid with a (C$_1$-C$_3$)alkanol, phenol or benzyl alcohol, it is preferred to prepare the desired ester from an acid in which the 3-hydroxy group is in protected form (e.g., as the t-butyldimethyl silyl ether derivative), so as to avoid potential dimerization/polymerization as a side reaction. Such a protecting group is removed by mild acid hydrolysis, or treatment with fluoride ion, during isolation of the ester, or as a final step, care being taken to avoid acid conditions sufficiently vigorous to hydrolyze the desired ester group.

Mixed anhydrides are well-suited as the activated acid form in the preparation of said alkyl, phenyl and benzyl esters. Generally, the acids are first converted in situ to a tertiary amine salt in the presence of a 1 to 1.1 molar excess of the amine. A variety of tertiary amines are suitable for this purpose. Exemplary are triethylamine, N-methyl-piperidine, N-methylmorpholine, dimethylaniline or quinoline. Suitable inert solvents are methylene chloride, chloroform, dimethylformamide, and dimethyl-acetamide. It is preferrable that the acid be completely dissolved by the excess of tertiary amine, which may require a stirring period, together with gentle warming, if necessary. The solution of amine salt is then reacted with an equivalent of alkyl (e.g. ethyl), benzyl, or phenyl chloroformate, at a temperature in the range of −40° to 25° C., preferably in the range −10° to 10° C., to form a mixed anhydride in solution. Without isolation, the mixed anhydride is reacted directly with the appropriate alcohol or phenol to yield the desired ester. The reaction is usually initiated at a cool temperature (such as −40° to 15° C.), but allowed to warm to higher temperature (such as 15° to 40° C.) to complete the reaction.

The above alkyl and benzyl esters are alternatively prepared, and the esters wherein R is a conventional radical forming an ester which is hydrolyzable under physiological conditions are generally prepared, by reaction of a salt of the acid (I, R=H; preferably the tetrabutylammonium salt) with an appropriate compound containing a displaceable halide (iodide, bromide or chloride; generally preferred, where available, in that order), or another group suitable for nuclophilic displacement. Exemplary are CH$_3$OSO$_2$CH$_3$, C$_2$H$_5$Br, CH$_3$CH$_2$CH$_2$I, ICHR$^1$OCOR$^2$, ICHR$^1$OCOOR$^2$,

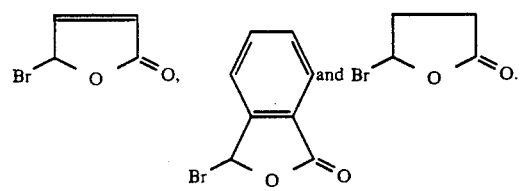

The required salt can be in isolated form, or more conveniently, formed in situ from the acid by use of at least one equivalent of a base. The reaction is carried out in a reaction-inert solvent, preferably one which is essentially anhydrous. A particularly convenient reaction system employs excess potassium carbonate as base in acetone as solvent. When the halide is chloro or bromo, up to three or more equivalents of anhydrous sodium iodide is added, if desired, to enhance the rate of reaction. An excess of the halide reagent is not critical to the reaction, but such an excess will generally be used in order to force the reaction to completion in a shorter period of time. The rate of reaction will also depend greatly on the halide (e.g., I>Br>Cl) and on the nature of the radical group R (e.g., more branched ICHCH$_3$OCOCH$_3$ will react more slowly than ICH$_2$OCOCH$_3$). The reaction temperature is not critical, a temperature in the range of 0°-100° C. being generally satisfactory.

The required hydroxy protected anhydride is available according to the method of Rosen et al., J. Org. Chem., vol. 49, pp. 3657-3659 (1984).

The required amines of the formula (II) are available by conventional methods from the corresponding aldehyde (e.g., by reductive alkylation, or by hydride reduction of the corresponding oxime, as exemplified in Preparations below). The required aldehydes are prepared according to procedures described by Willard et al., loc. cit. and Stokker et al., loc. cit.

The biological procedures for evaluating these compounds were as follows: Rat liver microsomal, HMG-CoA (3-hydroxy-3-methylglutaryl-coenzyme A) reductase was isolated, solubilized and purified through the heat fractionation methods of Rogers et al., Analytical Biochemistry, vol. 101, pp. 107-111 (1980). HMG-CoA reductase activity was measured according to the procedure of Harwood et al., J. Lipid. Res., vol. 25, pp. 967-978 (1984). Inhibition of rat cholesterol biosynthesis was measured using $^{14}$C-acetate according to the procedure of Endo et al., Eur. J. Biochem., vol. 77, pp. 31–36 (1977).

For use in the treatment or prevention of atherosclerosis in a mammal, including man, a compound of the formula (I) is administered in a blood cholesterol lowering (or a low blood cholesterol maintaining) amount of about 1–50 mg/kg/day, in single or divided daily doses. In particular cases, dosages outside that range are prescribed at the discretion of the attending physician. The preferred route of administration is generally oral, but parenteral administration (e.g. intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

4-[(4'-Fluoro-3,3',5-trimethylbiphen-2-yl)-methylcarbamoyl]-3-[(t-butyldimethylsilyl)oxy]-butyric Acid To a −60° C. solution of 2-aminomethyl-4-fluoro-3,3'5-trimethylbiphenyl (2.30 g, 9.45 mmol), 4-dimethylaminopyridine (0.175 g, 1.43 mmol) and triethylamine (0.508 g, 5.00 mmol) in anhydrous methylene chloride (22 ml) was added 3-(t-butyldimethylsilyoxy) glutaric anhydride (2.43 g, 9.93 mmol). After stirring at −60° C. for 1 hour, the reaction was warmed to −20° C. for 1 hour, and then to 0° C. for an additional 16 hours. The reaction mixture was diluted with ether (50 ml), then washed with 1M phosphoric acid (22 ml) and saturated aqueous sodium bicarbonate (2×22 ml). The combined aqueous phases were acidified with phosphoric acid (65 ml) to a pH of 4, then extracted with ether (2×22 ml). The combined organic phases were dried with magnesium sulfate, filtered and concentrated in vacuo to give 4.783 g (quantitative yield) of crude product. A portion of this material (1.50 g) was purified by flash chromatography (1:1 methanol:ethyl acetate) to give 1.472 g of purified title product.

High resolution mass spectra: m/e found 487.2610, calc. for $C_{27}H_{38}FNO_4Si$ 487.2554. $^1$H-NMR (CDCl$_3$), delta 10.20 (br, s, 1 H); 7.06–6.94 (m, 4 H); 6.84 (s, 1 H); 6.37 (t, 5 Hz, 1 H); 4.41 (pentet, 6 Hz, 1 H); 4.27 (d, 5 Hz, 2 H); 2.51 (d, 6 Hz, 4 H); 2.33 (s, 3 H); 2.28 (s, 3 H); 2.27 (d, 2 Hz, 3 H); 0.66 (s, 9H); 0.01 (s, 3 H); −0.03 (s, 3 H). $^{13}$C-NMR (CDCl$_3$), delta: 174.2, 170.7, 162.3, 159.0, 142.5, 137.8, 137.4, 137.0, 136.9, 132.0, 131.9, 130.8, 129.5, 128.8, 127.8, 127.7, 124.7, 124.5, 114.9, 114.6, 66.6, 42.8, 38.8, 29.7, 25.4, 20.9, 19.6, 17.6, 14.6, 14.6 (fluorine not decoupled). IR (CHCl$_3$) cm$^{-1}$: 3520, 3450, 3370, 2980, 2950, 2930, 2860, 1715, 1660, 1620, 1495, 1465.

EXAMPLE 2

4-[(4'-Fluoro-3,3',5-trimethylbiphen-2-yl)-methylcarbamoyl]-3-hydroxybutyric Acid A solution of 20% hydrofluoric acid in acetonitrile (54 ml) was added to a suspension of the title product of the preceding Example (2.69 g, 5.52 mmol) in acetonitrile (215 ml). The resulting mixture was stirred for 20 hours. The reaction mixture was then neutralized by adding solid sodium bicarbonate with vigorous stirring. The resulting suspension was filtered through a pad of solid sodium bicarbonate and concentrated in vacuo to give 3.153 g of a yellow solid. This solid was dissolved in water (80 ml). The resulting mixture was basified with saturated aqueous sodium bicarbonate (10 ml) to a pH of 10 and extracted with ethyl acetate (3×20 ml). The aqueous phase was then acidified with 1N hydrochloric acid 915 ml) to a pH of 2 and extracted with ethyl acetate (2×20 ml). The combined extracts were dried over magnesium sulfate, filtered and concentrated to give 0.294 g (14% yield) of present title product; mp 152°–154° C.

High resolution mass spectra: m/e found 373.1681, calc. for $C_{21}H_{24}FNO_4$ 373.1689. $^1$H-NMR (CDCl$_3$), delta: 7.13–6.93 (m, 4 H); 6.89 (s, 1 H); 6.50 (t, 5 Hz, 1 H), 4.39–4.26 (m, 1 H); 4.22 (d, 5 Hz, 2 H); 2.48 (d, 6 Hz, 2 H); 2.41–2.21 (m, 11 H); 2.08 (s, 1H). $^{13}$C-NMR (CDCl$_3$), delta: 173.5, 170.9, 142.6, 138.1, 136.8, 132.0, 131.9, 130.4, 130.0 128.5, 127.8, 127.7, 124.0, 114.6, 114.2, 41.7, 41.2, 38.7, 20.8, 19.4. IR (CHCl$_3$) cm$^{-1}$: 3300, 2960, 2930, 1710, 1630, 1540, 1505, 1475.

EXAMPLE 3

By the methods of Examples 1–2, the aminomethyl derivatives of Preparation 3 are converted to the corresponding 4-[(substituted-biphen-2-yl)methyl carbamoyl]-3-hydroxybutyric acids.

EXAMPLE 4

Ethyl 4-[(4'-Fluoro-3,3',5-trimethyl-biphen-2-yl)methylcarbamoyl]-3-[(t-butyldimethylsilyl)oxy]butyrate Title product of Example 1 (1.95 g, 4 mmol) is dissolved in 40 ml of methylene chloride and triethylamine (1.12 ml, 8 mmol), with warming to 40° C., if necessary, and then cooled to 0°–5° C. Ethyl chloroformate (0.39 ml, 4.1 mmol) diluted with 5 ml of CH$_2$Cl$_2$ is added at a rate which maintains a temperature of 0°–5° C. and the mixture stirred for 1 hour after addition is complete. Finally, anhydrous ethanol (0.25 ml, 4.2 mmol) diluted with 5 ml of CH$_2$Cl$_2$ is added over 5 minutes, and the mixture warmed to 20°–25° C. and stirred overnight. The reaction mixture is washed in sequence with 25 ml 1M phosphoric acid, 25 ml saturated NaHCO$_3$ and 25 ml water, dried (MgSO$_4$) and stripped in vacuo to yield title product.

Substituting a molar equivalent of methanol, isopropanol, phenol or benzyl alcohol in this process produces the corresponding methyl, isopropyl, phenyl or benzyl ester, respectively.

EXAMPLE 5

Ethyl 4-[(4'-Fluoro-3,3',5-trimethylbiphen-2-yl)methylcarbamoyl]-3-hydroxybutyrate The product of the preceding example is deprotected with HF/CH$_3$CN according to the method of Example 2. To purify, the crude product is taken into ethyl acetate, extracted with 1M phosphoric acid, saturated NaHCO$_3$ and water, dried and restripped.

By the same method the other 3-hydroxy protected esters of the preceding Example are converted to the corresponding methyl, isopropyl, phenyl and benzyl esters.

EXAMPLE 6

Pivaloyloxymethyl 4-[(4'-Fluoro-3,3',5-trimethylbiphen-2-yl)methylcarbamoyl]-3-hydroxybutyrate Tetrabutylammonium hydrogen sulfate (0.374 g, 1.1 mmol) is dissolved in 2.5 ml H$_2$O. NaHCO$_3$ (92 mg, 1.1 mmol) is added portionwise at a rate which controls foaming. Finally, title product of Example 2 (0.41 g, 1.1 mmol) is added. After about 30 minutes of stirring, the solution is extracted 4×5 ml CHCl$_3$ and the combined extracts dried and stripped to yield intermediate tetrabutylammonium salt. Under nitrogen, the latter is dissolved in 2 ml acetone and chloromethyl pivalate (0.216 ml, 1.1 mmol) is added. After 24 hours, the acetone is stripped and the residue dissolved in 5 ml ethyl acetate, washed 3×5 ml water and 1×5 ml brine, dried and restripped to yield title product. The reaction rate is enhanced, and the reaction time shortened by the addition of NaI (0.15-0.30 g, 1-2 mmol) to the acetone reaction mixture and/or by using elevated temperatures (e.g., the reflux temperature of acetone).

The corresponding methyl, hexanoyloxymethyl, 1-(isobutyryloxy)ethyl, 1-(methoxycarbonyloxy)ethyl, isobenzofuran-3(1H)-on-1-yl (3-phthalidyl) and gamma-butyrolacton-4-yl (3,4-dihydrofuran-5(1H)-on-1-yl) esters are prepared by the same method, substituting a molar equivalent of methyl iodide, chloromethyl hexanoate, 1-chloroethyl isobutyrate, 3-bromophthalide, and 4-bromo-gamma-butyrolactone, respectively, for chloromethyl pivalate.

EXAMPLE 7

1-(Ethoxycarbonyloxy)ethyl 4-[(4'-Fluoro-3,3',5-trimethylbiphen-2-yl)methylcarbamoyl]-3-hydroxybutyrate The title product of Example 2 (4.1 g, 0.011 mol), K$_2$CO$_3$ (3.0, 0.022 mol), 1-chloroethyl ethyl carbonate (5.0, 0.033 mol) and NaI (1.65 g, 0.011 mol) are combined in 60 ml of acetone and heated at reflux overnight. The reaction mixture is stripped in vacuo to a volume of 10 ml and then diluted with 100 ml each of H$_2$O and CH$_2$Cl$_2$. The organic layer is separated, washed with 100 ml H$_2$O, dried (Na$_2$SO$_4$) and stripped in vacuo to yield title product.

By the same method 5-bromofuran-2(5H)-one and chloromethyl pentanoate are converted, respectively, to the corresponding furan-5(1H)-on-1-yl and pentanoylmethyl esters.

PREPARATION 1

2-Methoxyiminomethyl-4'-fluoro-3,3',5-trimethylbiphenyl

Methoxylamine hydrochloride (0.190 g, 227 mmol) was added to a solution of 4'-fluoro-3,3',5-trimethylbiphenyl-2-carbaldehyde (0.500 g, 2.06 mmol), in pyridine (5.0 ml). The reaction mixture was stirred for 17 hours and then concentrated in vacuo to give 1.068 g of a yellow oil. Water (1.0 ml) was added and the resulting suspension was extracted with ether (3×1.0 ml). The combined extracts were dried over magnesium sulfate, filtered and concentrated in vacuo to give 0.588 g (99% yield) of title product.

High resolution mass spectra m/e found 271.1329, calc. for C$_{17}$H$_{18}$FNO 271.1372. $^1$H-NMR (CDCl$_3$), delta: 7.98 (s, 1 H); 7.15-7.01 (m, 4 H); 6.96 (s, 1 H); 3.92 (s, 3 H); 2.58 (s, 3 H); 2.38 (s, 3 H); 2.34 (s, 3 H). $^{13}$C-NMR (CDCl$_3$), delta: 162.4, 149.0, 142.4, 138.4, 137.8, 136.5, 136.4, 132.8, 132.7, 131.3, 128.7, 128.6, 128.5, 125.7, 124.6, 124.4, 114.7, 114.4, 61.8, 22.5, 21.1, 14.6, 14.5. IR (CHCl$_3$) cm$^{-1}$: 2980, 2950, d 2920, 2830, 1615, 1510, 1470, 1450.

PREPARATION 2

2-Aminomethyl-4'-fluoro-3,3',5-trimethylbiphenyl

A solution of the title product of the preceding Preparation (3.29 g, 12.1 mmol) in anhydrous tetrahydrofuran (25 ml) was added dropwise with stirring to a suspension of lithium aluminum hydride (0.619 g, 16.3 mmole) in (50 ml). The resulting mixture was refluxed for 2 hours, then allowed to cool room temperature. The reaction was quenched by successive addition of water (1.0 ml), 15% aqueous sodium hydroxide (1.0 ml) and water (3.0 ml). The precipitate that formed was collected by filtration and washed with ether (50 ml). The combined filtrates were concentrated in vacuo to give 2.889 g of a yellow oil. Purification by flash chromatography (toluene) gave 2.41 g (82% yield) of title product.

High resolution mass spectra: m/e found 243.1425 calc. for C$_{16}$H$_{18}$FN 243.1424. $^1$H-NMR (CDCl$_3$), delta: 7.17-6.96 (m, 4 H); 6.87 (s, 1 H); 3.71 (s, 2 H); 2.45 (s, 3 H); 2.33 (s, 3 H); 2.31 (s, 3 H); 1.17 (s, 2 H). $^{13}$C-NMR (CDCl$_3$), delta: 162.8, 158.9, 141.5, 137.8, 137.7, 136.6. 136.1, 136.0, 132.2, 132.1, 130.8, 128.8, 127.9, 127.8, 124.5, 124.3, 114.7, 114.4, 40.3, 20.9, 19.5, 14.7, 14.6. IR (CHCl$_3$) cm$^-$: 3360, 2940, 2910, 2870, 1595, 1490, 1465.

PREPARATION 3

By the methods of Preparations 1 and 2, the following additional 2-(aminomethyl)biphenyls are prepared from the appropriately substituted biphenyl-2-carbaldehyde:
2-(Aminomethyl)-3,5-dichlorobiphenyl;
2-(Aminomethyl)-3,4',5-trichlorobiphenyl;
2-(Aminomethyl)-3,5-dichloro-3'-methylbiphenyl;
2-(Aminomethyl)-3,5-dichloro-3,5'-dimethylbiphenyl;
2-(Aminomethyl)-3,5-dichloro-4'-fluorobiphenyl;
2-(Aminomethyl)-3,5-dichloro-4'-fluoro-2'-methylbiphenyl;
2-(Aminomethyl)-3,5-dichloro-3'-ethylbiphenyl;
2-(Aminomethyl)-3,5-dichloro-3'-methylbiphenyl;
2-(Aminomethyl)-3,3',5,5'-tetrachlorobiphenyl;
2-(Aminomethyl)-3,3',4,5-tetrachlorobiphenyl;
2-(Aminomethyl)-3,5-dichloro-2'-methylbiphenyl;
2-(Aminomethyl)-3,5-dichloro-3'-methoxybiphenyl;
2-(Aminomethyl)-3,5-dichloro-4'-methoxybiphenyl;

2-(Aminomethyl)-3,5-dichloro-3'-fluorobiphenyl;
2-(Aminomethyl)-5-chloro-4'-fluoro-3,3'-dimethylbiphenyl;
2-(Aminomethyl)-3',4'-dichloro-3,5-dimethylbiphenyl;
2-(Aminomethyl)-3,3',5,5'-tetramethylbiphenyl;
2-(Aminomethyl)-4'-fluoro-3,5-dimethylbiphenyl;
2-(Aminomethyl)-3',4'-dichloro-3,6-dimethylbiphenyl;
2-(Aminomethyl)-3-chloro-4'-fluoro-3'-methylbiphenyl;
2-(Aminomethyl)-3,5-dichloro-4'-methylbiphenyl;
2-(Aminomethyl)-3,5-dichloro-4'-methoxybiphenyl; and
2-(Aminomethyl)-3,5-dichloro-3'-fluorobiphenyl.

I claim:

1. A compound having the formula

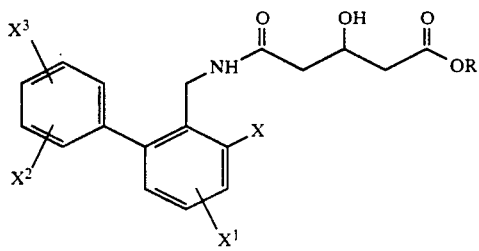

wherein
R is hydrogen, $(C_1-C_3)$alkyl, phenyl, benzyl or a conventional radical forming an ester group which is hydrolyzable under physiological conditions;
X is F, Cl, Br, I, $(C_1-C_3)$alkyl, $CF_3$, benzyl, $(C_1-C_3)$alkoxy, $(C_2-C_4)$alkanoyloxy or $(C_2-C_4)$alkoxycarbonyl; and
$X^1$, $X^2$ and $X^3$ are each independently hydrogen, F, Cl, Br, I, $(C_1-C_3)$alkyl, $CF_3$, benzyl, $(C_1-C_3)$alkoxy, $(C_2-C_4)$alkanoyloxy or $(C_2-C_4)$alkoxycarbonyl; or
a pharmaceutically acceptable cationic salt thereof when R is hydrogen.

2. A compound of claim 1 wherein R is a radical selected from the group consisting of:
furan-5(1H)-on-1-yl;
isobenzofuran-3(1H)-on-1-yl;
3,4-dihydrofuran-5(1H)-on-1-yl;
—$CHR^1OCOR^2$, and
—$CHR^1OCOOR^2$;
wherein
$R^1$ is hydrogen or methyl; and
$R^2$ is $(C_1-C_6)$alkyl.

3. A compound of claim 1 wherein R is hydrogen, $(C_1-C_3)$alkyl, phenyl or benzyl.

4. A compound of claim 3 wherein R is hydrogen.

5. The compound of claim 4 wherein X is 3-methyl, $X^1$ is 5-methyl, $X^2$ is 3'-methyl and $X^3$ is 4'-fluoro.

6. A pharmaceutical composition for the treatment or prevention of atherosclerosis in a mammal which comprises a blood cholesterol lowering effective amount of a compound of claim 1.

7. A pharmaceutical composition for the treatment or prevention of atherosclerosis in a mammal which comprises a blood cholesterol lowering effective amount of a compound of claim 4.

8. A pharmaceutical composition for the treatment or prevention of atherosclerosis in a mammal which comprises a blood cholesterol lowering effective amount of the compound of claim 5.

9. A method of treating or preventing atherosclerosis in a mammal which comprises administering a blood cholesterol lowering effective amount of a compound of claim 1 to said mammal.

10. A method of treating or preventing atherosclerosis in a mammal which comprises administering a blood cholesterol lowering effective amount of a compound of claim 4 to said mammal.

11. A method of treating or preventing atherosclerosis in a mammal which comprises administering a blood cholesterol lowering effective amount of the compound of claim 5 to said mammal.